(12) United States Patent
Strom et al.

(10) Patent No.: US 6,410,008 B1
(45) Date of Patent: Jun. 25, 2002

(54) CHIMERIC IL-10 PROTEINS AND USES THEREOF

(75) Inventors: Terry B. Strom; Xin Xiao Zheng, both of Brookline; Alan Steele, Wellesley, all of MA (US)

(73) Assignee: Beth Israel Hospital Association, Boston, MA (US)

( * ) Notice: Subject to any disclaimer, the term of this patent is extended or adjusted under 35 U.S.C. 154(b) by 0 days.

(21) Appl. No.: 08/355,502

(22) Filed: Dec. 12, 1994

(51) Int. Cl.$^7$ ................... C07K 14/54; A61K 38/20; C12N 15/24
(52) U.S. Cl. .................. 424/85.2; 530/351; 530/402; 514/2; 514/8; 514/12; 435/69.7; 435/71.2; 435/320.1; 435/252.3
(58) Field of Search ................... 424/85.1, 85.2; 530/351, 402; 514/2, 8, 12; 435/69.1, 69.2, 240.2, 252.3, 320.1, 69.7, 71.1, 71.2, 254.11, 325, 471; 935/11, 22, 27, 66, 70

(56) References Cited

U.S. PATENT DOCUMENTS

| | | | | |
|---|---|---|---|---|
| 5,116,964 A | * | 5/1992 | Capon et al. | 536/27 |
| 5,196,321 A | * | 3/1993 | Bachmair et al. | 435/69.7 |
| 5,231,012 A | * | 7/1993 | Mosmann et al. | 435/69.52 |
| 5,428,130 A | * | 6/1995 | Capon et al. | 530/350 |
| 5,447,851 A | * | 9/1995 | Beutler et al. | 435/69.7 |

FOREIGN PATENT DOCUMENTS

| | | |
|---|---|---|
| CA | 2045869 | 6/1991 |
| EP | WO 90 07932 A | 7/1990 |
| EP | 0 464 533 A | 1/1992 |
| EP | WO 94 04180 A | 3/1994 |
| WO | 8807089 * | 9/1988 |
| WO | WO 92/12725 | 8/1992 |

OTHER PUBLICATIONS

Bowie et al. (1990) Science, vol. 247, pp. 1306–1310.*
Capon et al. (1989) Nature, vol. 337, pp. 525–531.*
Bone, R.; "The Pathogenesis of Sepsis," *Annals of Internal Medicine*, 115:457–469 (1991).
Byrne, et al.; "Adult Respiratory Distress Syndrome", *Acute Care*, 13:206–234 (1987).
D'Andrea, et al.; "Interleukin 10 (IL–10) Inhibits Human Lymphocyte Interferon γ–Production by Suppressing Natural Killer Cell Stimulatory Factor/IL–12 Synthesis . . . ", *J. Exp. Med*. 178:1041–1048 (1993).
de Waal Malefyt, et al.; "Interleukin 10 (IL–10) and Viral IL–10 Strongly Reduce Antigen–specific Human T–Cell Proliferation by Diminishing the Antigen–presenting . . . ", *J. Exp. Med*. 174: 915–924 (1991).
Duncan, et al.; "Localization of the binding site for the human high–affinity Fc receptor on IgC", *Nature* 332:563–564 (1988).
Duncan, et al.; "The binding site for Clq on IgG", *Nature* 332:738–740 (1988).
Fiorentino, et al.; "IL–10 Acts on the Antigen–Presenting Cell to Inhibit Cytokine Production by Th1 Cells," *The Journal of Immunology* 146;3444–3451 (1991).
Fiorentino, et al.; "IL–10 Inhibits Cytokine Production by Activated Macrophages," *The Journal of Immunology* 147:3815–3822 (1991).
Gerard, et al.; "Interleukin 10 Reduces the Release of Tumor Necrosis Factor and Prevents Lethality in Experimental Endotoxemia," *J. Exp. Med*. 177:547–550 (1993).
Glauser, et al.; "Septic shock: pathogenesis," *The Lancet* 338:732–736 (1991).
Hsu, et al.; "Differential effects of IL–4 and IL–10 on IL–2–induced IFN–γ synthesis and lymphokine–activated killer activity," *International Immunology* 4:563–569 (1992).
Lee, et al., "Pancreatic Islet Production of Murine Interleukin–10 Does Not Inhibit Immune–Mediated Tissue Destruction," *The Journal of Clinical Investigation*, 93:1332–1338 (1994).
Mathison, et al., "Participation of TUmor Necrosis Factor in the Mediation of Gram Negative Bacterial Lipopolysaccharide–induced Injury in Rabbits," *The Journal of Clinical Investigation*, 81:1925–1937 (1988).
Moore, et al., "Homology of Cytokine Synthesis Inhibitory Factor (IL–10) to the Epstein–Barr Virus Gene BCRFI," *Science* 248:1230–1234 (1990).
Moore, et al., "Interleukin–10," *Annu. Rev. Immunol*. 11:165–190 (1993).
Thompson–Snipes, et al., "Interleukin–10: A Novel Stimulatory Factor for Mast Cells and Their Progenitors" *J. Exp. Med*. 173:507–510 (1991).
Steele, Alan W. et al., "Structure and function in vitro and in vitro and in in vivo of a family of murine interleukin–2Fc . . . ", J. American Soc. of Nephr., vol. 4, p. 636 (1993).
Traub A. et al., "Interferon albumin conjugate with conserved biological activity", J. of General Virology 53: 389–92 (1981).

* cited by examiner

*Primary Examiner*—Prema Mertz
(74) *Attorney, Agent, or Firm*—Fish & Richardson P.C.

(57) ABSTRACT

Disclosed are chimeric proteins having IL-10 fused to an enzymatically inactive polypeptide which increases the circulating half-life of IL-10. The chimeric polypeptides are useful for treating or preventing septic shock, inhibiting the development of Type I diabetes, and treating multiple myeloma in a patient.

7 Claims, 6 Drawing Sheets

CHIMERIC IL-10 PROTEINS AND USES THEREOF

STATEMENT AS TO FEDERALLY SPONSORED RESEARCH

Figure 1:
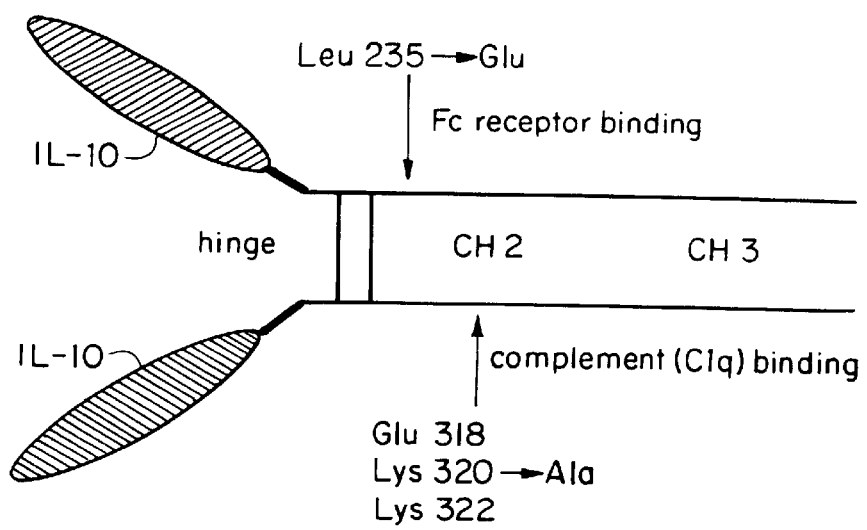

This invention was made at least in part with funds from the Federal government, and the government therefore has certain rights in the invention.

BACKGROUND OF THE INVENTION

This invention relates to chimeric proteins including interleukin-10, and therapeutic uses thereof.

Interleukin-10 (IL-10) is a cytokine produced by activated Th2 cells, B cells, keratinocytes, monocytes and macrophages (Moore et al., Annu. Rev. Immunol. 11:165 (1993)). In vitro, murine and human IL-10 inhibit cytokine synthesis by Th1 cells, natural killer cells, monocytes, and macrophages (Fiorentino et al., J. Exp. Med., 170:2081–2095 (1989); Fiorentino et al., J. Immunol. 146:3444 (1991); Hsu et al., Int. Immunol. 4:563 (1992); Hsu et al., Int. Immunol. 4:563 (1992); D'Andrea et al., J. Exp. Med. 178:1041 (1993); de Waal Malefyt et al., J. Exp. Med. 174:915 (1991); Fiorentino et al., J. Immunol. 147:3815 (1991)).

Gram-negative septicemia in hospitalized patients is invariably associated with high morbidity and mortality (Bone, Ann. Intern. Med. 115:457 (1991)). Case fatality rates of 20–60% reflect the frequent development of acute lung injury (Byrne et al., Acute Care 13:206 (1987)) and multiple organ failure (Abrams et al., Surg. Rounds 12:44 (1989)), as well as the lack of effective therapies. Endotoxin (LPS), a product of gram-negative bacteria, is a major causative agent in the pathogenesis of septic shock (Glausner et al., Lancet 338:732 (1991)). A septic shock-like syndrome can be induced experimentally by a single injection of LPS into animals. Injection of IL-10 into mice inhibits secretion of tumor necrosis factor (TNF) in vivo and protects against the lethal effects of endotoxin (Gerard et al., J. Exp. Med. 177(2):547 (1993)); (de Waal Malefyt et al., J. Exp. Med. 174:915 (1991); Fiorentino et al., J. Immunol. 147:3815 (1991); Moore et al., Science 248:1230 (1990)). Naturally-occurring cytokines have short circulating half-lives; naturally-occurring IL-10 is therapeutically effective for approximately 30 minutes following administration (Gerard et al., J. Exp. Med. 177(2):547 (1993)).

SUMMARY OF THE INVENTION

We have discovered that the in vivo half-life of IL-10 can be increased by bonding IL-10 to an enzymatically inactive polypeptide, and we have discovered that the chimeric IL-10 protein is useful for treating septic shock, Type I diabetes, and multiple myeloma in mammals.

Accordingly, in one aspect, the invention features a chimeric protein having IL-10 bonded to an enzymatically inactive polypeptide which increases the circulating half-life of IL-10 in vivo by a factor of at least 10.

In one embodiment, the enzymatically inactive polypeptide includes the Fc region of an IgG molecule and lacks an IgG variable region of a heavy chain. The Fc region can include a mutation which inhibits complement fixation and Fc receptor binding by the protein, or it can be lytic, i.e., able to bind complement. The protein can also be used in a therapeutic composition formed by an admixture of the chimeric protein with a pharmaceutically acceptable carrier. The therapeutic composition is administered to a mammal to treat septic shock, to inhibit the development of Type I diabetes, or to treat multiple myeloma. Where the Fc region of the chimeric protein is lytic, the chimeric protein is particularly useful for treating multiple myeloma.

The invention offers several features and advantages: (1) the chimeric proteins of the invention have an extended circulating half life and provide long term protection; (2) the chimeric protein can be easily purified; and (3) some of the chimeric proteins are mutated such that they are defective for antibody-dependent cell-mediated cytotoxicity (ADCC) and complement directed cytolysis (CDC), thus making them useful for treating septic shock, type I diabetes or multiple myeloma without destroying the target cells.

Useful enzymatically inactive polypeptides are those which, when fused to IL-10, extend the circulating half-life of IL-10 by a factor of at least 10. Preferred inactive polypeptides include human serum albumin and the Fc region of IgG minus an IgG heavy chain variable region.

Other features and advantages of the invention will be apparent from the following description of the preferred embodiments thereof, and from the claims.

DETAILED DESCRIPTION

The drawings will first be briefly described.

Drawings

FIG. 1 is a schematic representation of the scheme used for the genetic fusion of murine IL-10 and murine Fcγ2a cDNAs to create a murine IL-10/Fc immunoligand. Mutations were made in the CH2 domain of a Fcγ2a fragment with site-directed mutagenesis to replace Glu 318, Lys 320, and Lys 322 with Ala residues; Leu 235 was replaced with Glu to render the IL-10 immunoligand ineffective in directing ADCC and CDC. The non-lytic chimeric protein is referred to hereinafter as "IL-10/Fc." The lytic chimeric protein (without the mutation) is referred to as "IL-10/Fc++."

FIG. 2 is a reproduction of a blot obtained in Western analysis of the IL-10/Fc structure. The SDS-polyacrylamide gels were run under reducing (lanes 2–4) and non-reducing (lanes 5–7) conditions. The Western blots were performed with antibodies directed against (A) mIgG Fc, or (B) mIL-10. For both (A) and (B), lane 1 was loaded with a high molecular weight protein standard; lanes 2 and 5 were loaded with mIgG2a; lanes 3 and 6 were loaded with IL-10/Fc++; and lanes 4 and 7 were loaded with IL-10/Fc--.

Figure 3:
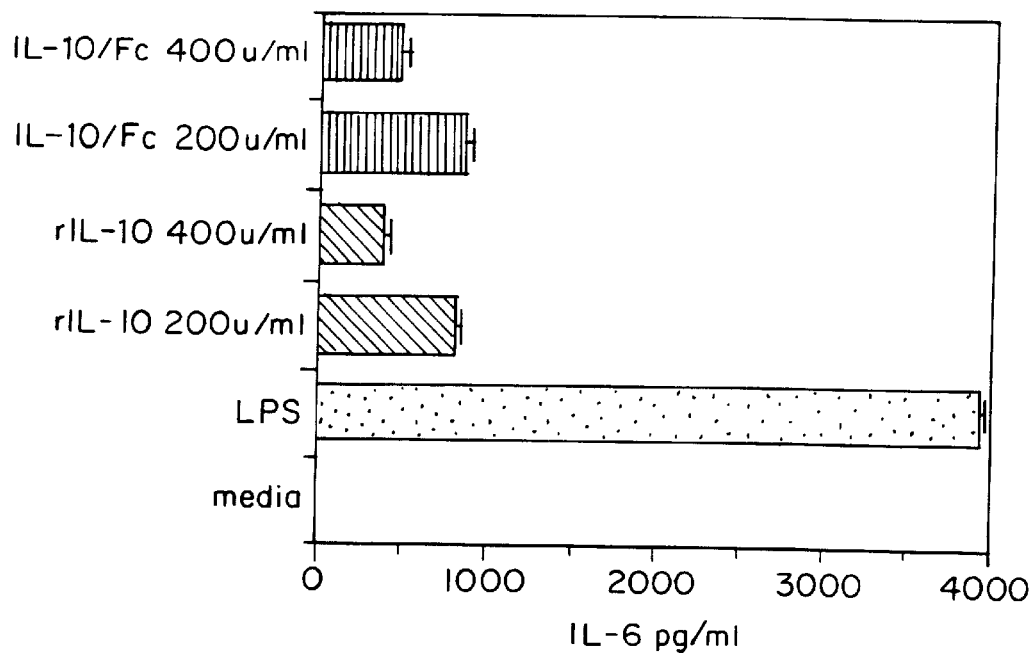

FIG. 3 is a histogram demonstrating that rIL-10 (wild-type, recombinant IL-10) and IL-10/Fc-- inhibit LPS-induced production of IL-6 by macrophages. PU5-1.8 cells ($10^6$ cells/ml) were pre-incubated with various concentrations of IL-10/Fc-- or rIL-10, as indicated, for 24 hours. LPS (10 µg/ml) then was added, and the cells were incubated for an additional 24 hours. Supernatants were collected and assayed for IL-6 concentration by ELISA.

Figure 4:
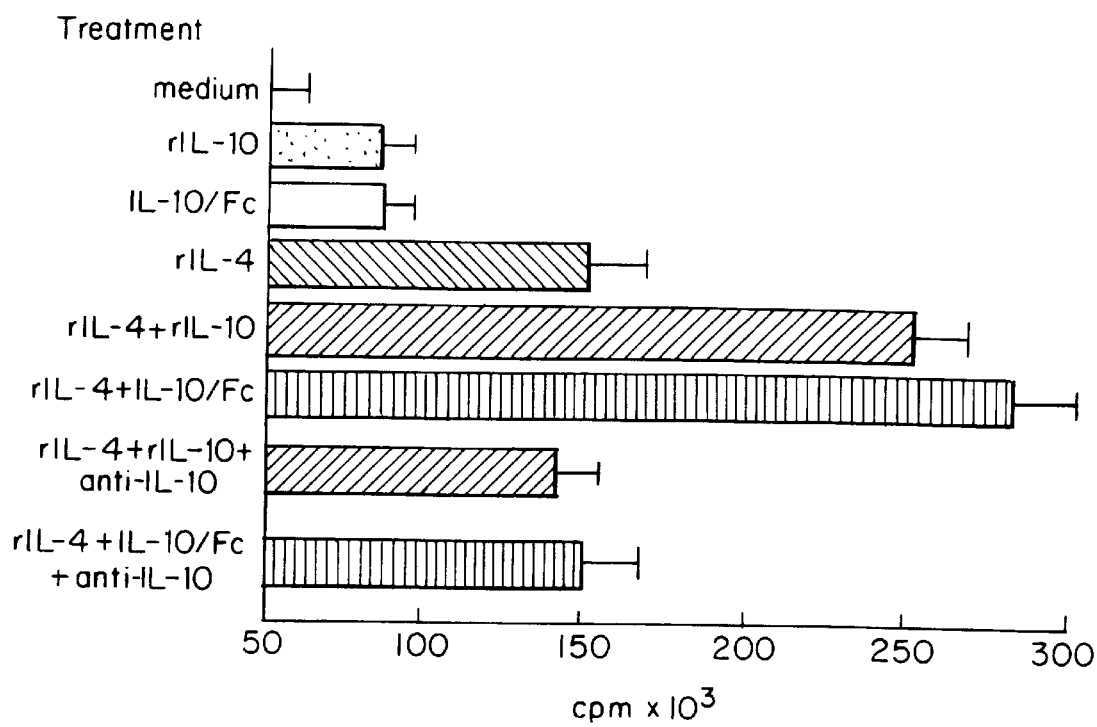

FIG. 4 is a histogram showing the costimulatory effects of IL-10/Fc-- on mast cell proliferation. The ability of rIL-10 or IL-10/Fc-- to enhance IL-4-dependent growth of MC/9 mast cells was assessed in a [$^3$H] thymidine incorporation assay. MC/9 mast cells ($5 \times 10^3$ cells/ml) were cultured for 3 days with rIL-10 (100 U/ml), IL-10/Fc-- (100 U/ml), rIL-4 (100 U/ml), or combinations of these factors in the presence or absence of a neutralizing anti-murine IL-10 mAb as indicated.

Figure 5:
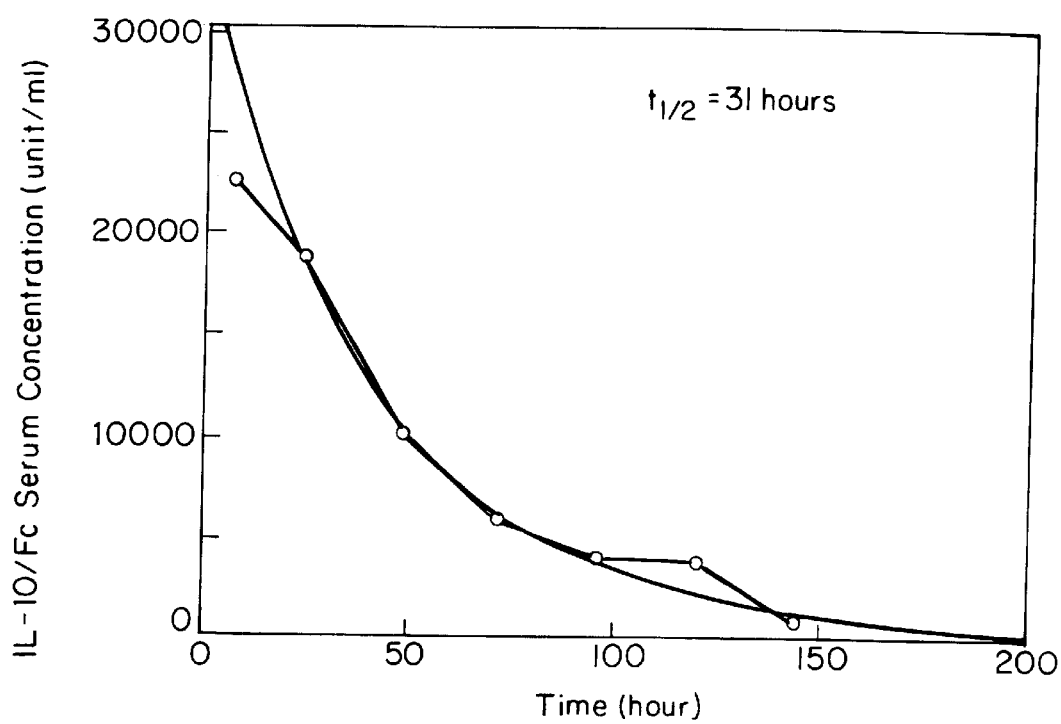

FIG. 5 is a plot of the IL-10/Fc-- circulating half-life. The time-related serum concentration of IL-10/Fc-- was determined following a single bolus intravenous dose (8 µg) of the chimeric protein. Blood samples were obtained by retro-orbital bleeding at the indicated intervals. IL-10/Fc-- levels were detected by ELISA with a rat-anti-mouse IL-10 mAb as the capture antibody and horseradish peroxide-conjugated rat anti-mouse IgG heavy chain mAb as the detection antibody.

Figure 6B:
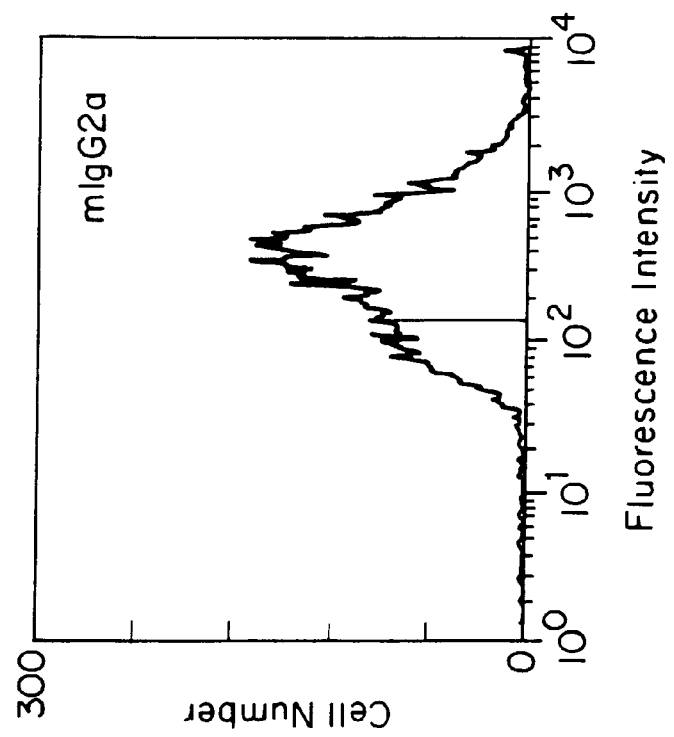
Figure 6A:
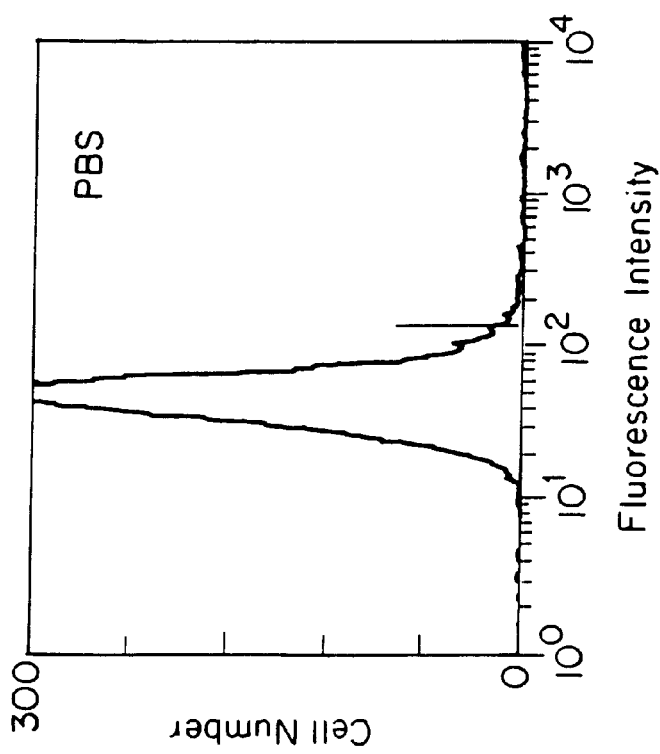
Figures 6C, 6D:
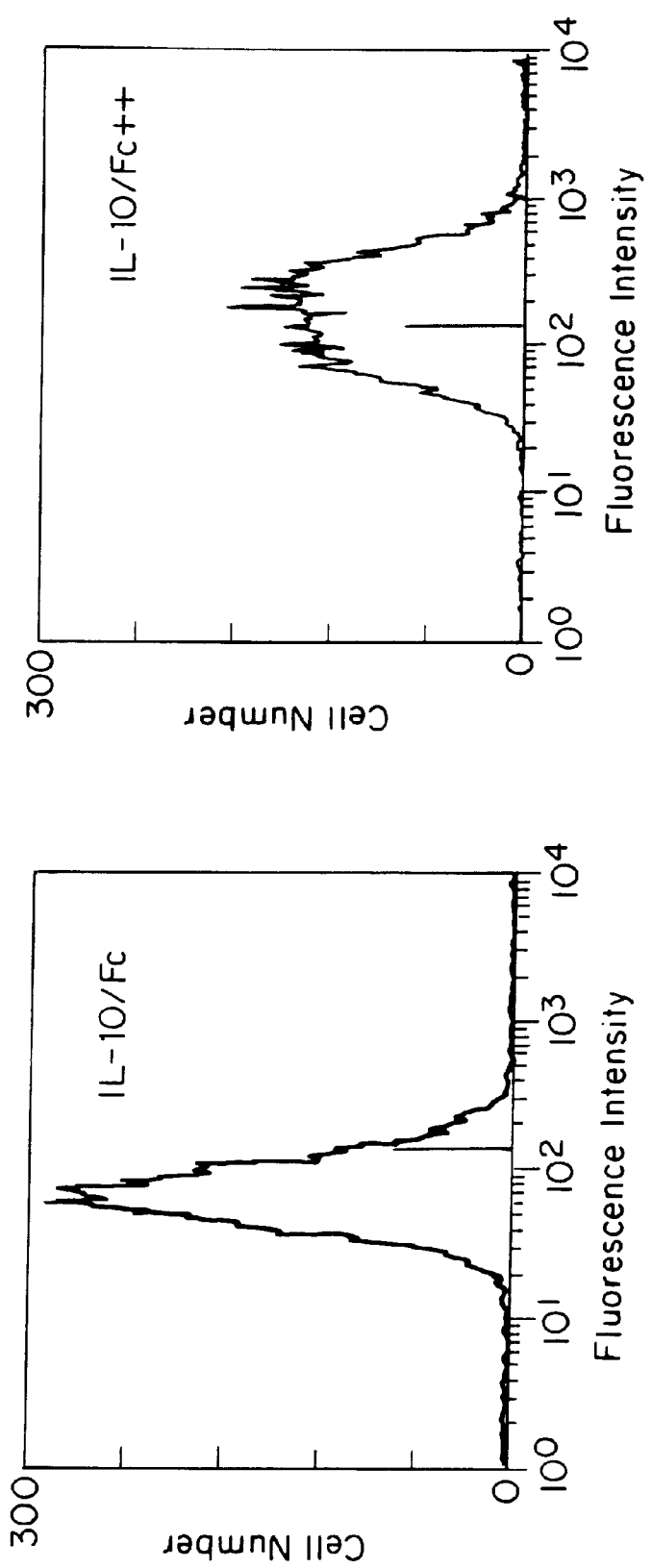

FIG. 6 is a series of FACS profiles indicating that, as is desired, IL-10/Fc-- exhibits poor FcγR I binding activity. FcγR I binding assays were performed using human FcγR I cDNA transfected CHO cells (murine FcγR I, FcγR II, and IL-10R negative). The FcγR I binding ability of IL-10/Fc++ and IL-10/Fc-- were analyzed by FACS.

Figure 7:
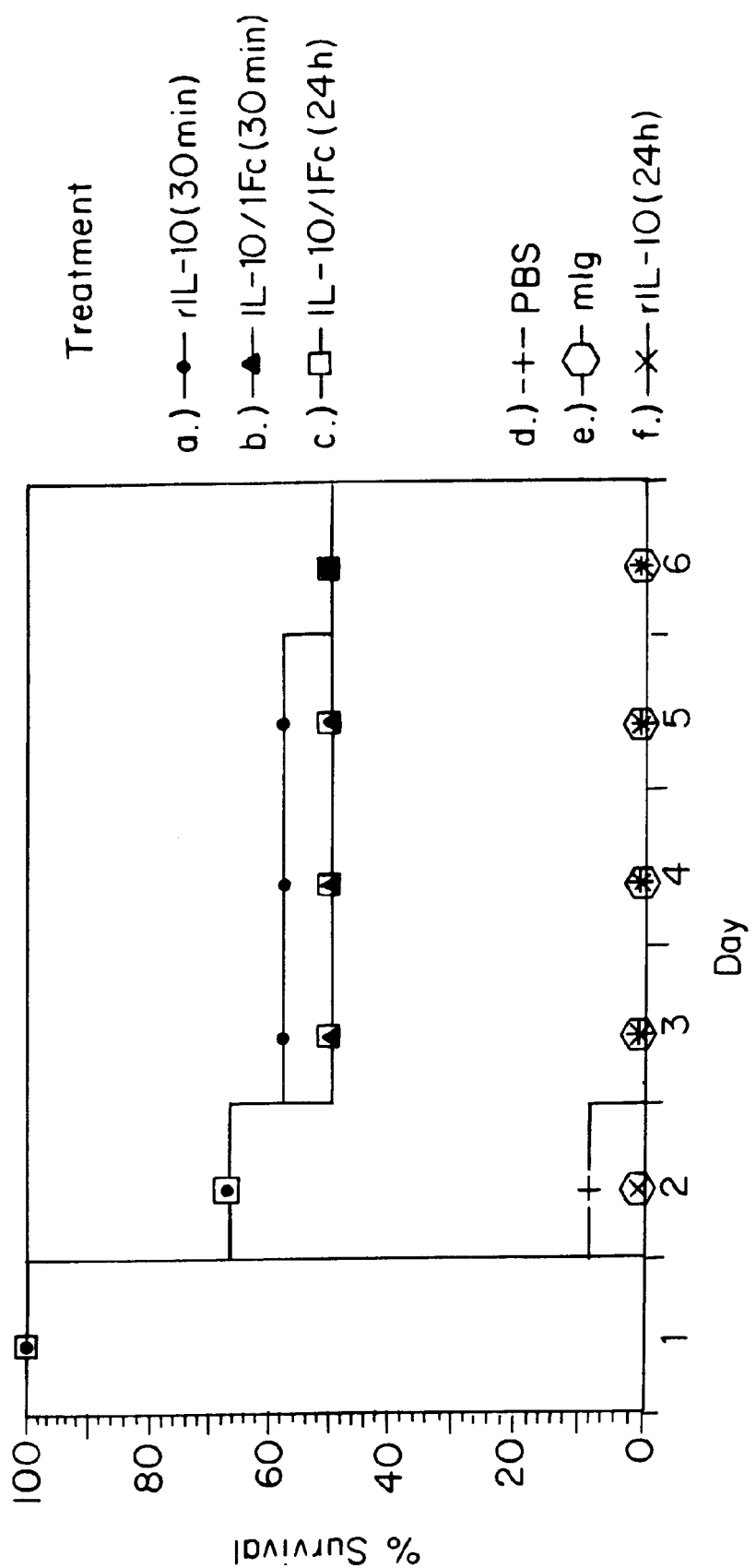

FIG. 7 is a plot showing that IL-10/Fc-- confers prolonged protection from the lethal effects of LPS in following an injection of 500 μg LPS. This plot shows the survival rates for the following six groups of BALB/c mice: (a) 12 mice pre-treated for 30 minutes with rIL-10; (b) 12 mice pre-treated for 30 minutes with 2000 U IL-10/Fc--; (c) 12 mice pre-treated for 24 hours with 4000 U IL-10/Fc--; (d) 12 mice pre-treated for 30 minutes with PBS; (e) 6 mice pre-treated for 30 minutes with 0.6 μg mIgG2a; (f) 12 mice pre-treated for 24 hours with 4000 U rIL-10.

ABBREVIATIONS

The following abbreviations are used herein:

| | |
|---|---|
| ADCC | antibody dependent cell-mediated cytotoxicity |
| CDC | complement directed cytolysis |
| CMV | cytolomegalovirus |
| Con A | concanavalin A |
| HBSS | Hank's balanced salt solution |
| PBS | phosphate-buffered saline |
| TNF | tumor necrosis factor |

Before providing a detailed working example of the invention, we now describe some of the parameters of the invention.

Chimeric IL-10 Proteins: Conventional molecular biology techniques can be used to produce chimeric proteins having IL-10 bonded to an enzymatically inactive polypeptide. The murine IL-10 gene has been described (Moore et al., 1990, Science 248: 1230–1234), and the human IL-10 gene has been cloned (see, e.g., U.S. Pat. No. 5,231,012, incorporated herein by reference). IL-10 can be truncated or mutated as long as it retains its biological activity. Preferably, the enzymatically inactive protein used in the production of the chimeric protein has, by itself, an in vivo circulating half-life greater than that of IL-10. More preferably, the half-life of the enzymatically inactive protein is at least 10 times that of IL-10. The circulating half-life of IL-10 can be measured in an ELISA of serum samples of animals carrying IL-10. In such ELISAs, antibodies directed against IL-10 can be used as the capture antibody, and antibodies directed against the enzymatically inactive protein can be used as the detection antibody. Such an ELISA can allow for the detection of only the chimeric IL-10 protein in a sample. A detailed working example of such an ELISA is provided herein.

Numerous polypeptides are suitable for use as an enzymatically inactive protein in the invention. Preferably, the protein has a molecular weight of at least 10 kD; a net neutral charge at pH 6.8; a globular tertiary structure; human origin; and no ability to bind to surface receptors other than the IL-10 receptor. Where the enzymatically inactive protein is IgG, preferably, the IgG portion is glycosylated.

The enzymatically inactive polypeptide used in the invention can include the Fc region of an IgG molecule and lack a variable region of an IgG heavy chain. A person skilled in molecular biology can readily produce such molecules from an IgG2a-secreting hybridoma (e.g., HB129) or other eukaryotic cells or baculovirus systems. If desired, the Fc region can be mutated to inhibit its ability to fix complement and bind the Fc receptor. For murine IgG Fc, substitution of Ala residues for Glu 318, Lys 320, and Lys 322 renders the protein unable to direct ADCC. Substitution of Glu for Leu 235 inhibits the ability of the protein to bind the Fc receptor. Appropriate mutations for human IgG also are known (see, e.g., Morrison et al., The Immunologist, 1994, 2: 119–124 and Brekke et al., The Immunologist, 1994, 2: 125). Other mutations can also be used to inhibit these activities of the protein, and art-known methods can be used assay for the ability of the protein to fix complement of bind the Fc receptor. Other useful enzymatically inactive proteins include human serum albumin, transferrin, enzymes such as t-PA which have been inactivated by mutations, and other proteins with a long circulating half-life.

The chimeric protein can be synthesized (e.g., in mammalian cells) using standard methods of recombinant protein expression. If desired, the chimeric protein can be affinity purified according to standard protocols with antibodies directed against IL-10. Antibodies directed against the enzymatically inactive protein are also useful for purifying the chimeric protein by standard immunoaffinity techniques.

Treatment or Prevention of Septic Shock: Septic shock in a mammal (e.g., a human) can be treated or prevented by administering to the mammal a therapeutically effective amount of a chimeric protein of the invention, either lytic or non-lytic form. The chimeric protein can be formulated in a pharmaceutically acceptable carrier, e.g., saline, for intravenous administration to the mammal. Generally, a dosage of 0.01 mg/kg to 500 mg/kg body weight is sufficient; preferably, the dosage is 10 μg/kg to 100 μg/kg. If desired, the efficacy of the treatment regimen can be assessed with conventional methods of monitoring patients for septic shock. Treatment is begun with the diagnosis or suspicion of septicemia or endotoxemia and is repeated at 12-hour intervals until stabilization of the patient's condition is achieved, on the basis of the observation that serum TNF levels are undetectable by ELISA.

Inhibition of the Development of Diabetes: The chimeric IL-10 proteins of the invention are also useful for inhibiting the development of Type I diabetes in a patient. The following detailed example employs a well-known animal model, the non-obese diabetic (NOD) mouse. I have found that administration of IL-10/Fc to NOD mice completely prevents the development of diabetes in these mice. IL-10/Fc (1 μg) was administered by intraperitoneal injection into 6 week old mice. When the mice reached 25 weeks of age, 80% of the control animals displayed signs of Type I diabetes, while none of the animals treated with IL-10/Fc appeared diabetic. Administration of IL-10/Fc to the mice was carried out every other day and then discontinued at 25 weeks of age. At 52 weeks of age, 84% of the animals which had been treated with IL-10/Fc continued to have normal glucose levels (i.e., they did not develop diabetes) despite the cessation of therapy. These data indicate that IL-10/Fc provides long-term protection against diabetes.

The chimeric IL-10 molecules of the invention can be administered to human patients to inhibit the development of diabetes. The chimeric molecule can be formulated for intraperitoneal, intravenous, subcutaneous, or intramuscular administration in a pharmaceutically acceptable carrier (e.g., saline). Preferably the therapeutic composition is administered to the patient upon discovery of anti-beta cell autoimmunity and/or subtle pre-diabetic changes in glucose metabolism (i.e., blunted early i.v. glucose tolerance test), and administration is repeated every other day or at a frequency as low as once per week. The preferred dosage of the chimeric protein can be determined by using standard techniques to monitor glucose levels, anti-beta cells autoantibody level, or abnormalities in glucose tolerance tests of the human being treated. A dosage of 1 µg to 500 mg/kg body weight is sufficient. Generally, the preferred dosage is 1 to 200 µg/kg; more preferably, the dosage is approximately 50 µg/kg.

Treatment of Cancer: The lytic chimeric proteins of the invention are useful for treating a number of cancers, e.g., multiple myeloma, in a human patient. Naturally-occurring IL-10 is known to inhibit the production of IL-6 and tumor necrosis factor (TNF). Multiple myeloma is a malignant plasma cell disorder in which IL-6 functions as an autocrine growth factor for many of the cells involved. In addition, multiple myeloma cells bear IL-10 receptors and thus the IL-10 portion of the chimeric protein targets the protein to the cancer cells which are then lysed by the lytic Fc portion. In this aspect of the invention, a therapeutic composition of a pharmaceutically acceptable carrier and a chimeric IL-10 protein (i.e., IL-10/Fc++) is administered to a patient diagnosed with multiple myeloma. The therapeutic composition can be administered intravenously.

There now follows a detailed example of the use of a chimeric protein of the invention to prevent septic shock in a mammal.

Genetic Construction of IL-10/Fc: cDNAs for murine IL-10 and murine Fcγ2a were generated from mRNA extracted from concanavalin (Con A) stimulated murine splenic cells (C57BL/6J; Jackson Laboratory, Bar Harbor, Me.) and an IgG2a secreting hybridoma (American Type Culture Collection HB129, Rockville, Md.), respectively, using standard techniques with reverse transcriptase MMLV-RT (Gibco BRL, Grand Island, N.Y.) and a synthetic oligo-dT$_{(12-18)}$ oligonucleotide (Gibco BRL). The IL-10 cDNA was then amplified by PCR using IL-10-specific synthetic oligonucleotides. The 5' oligonucleotide inserts a unique Not I restriction site 40 nucleotides 5' to the translational start codon, while the 3' oligonucleotide eliminates the termination codon and changes the C-terminal serine codon from AGC to TCG to accommodate the creation of a unique Bam HI site at the IL-10/Fc junction. Synthetic oligonucleotides used for the amplification of the Fcγ2a domain cDNA change the first codon of the hinge from Glu to Asp in order to create a unique Bam HI site spanning the first codon of the hinge and introduce a unique Xba I site 3' to the termination codon.

To make the construct for the nonlytic IL-10/Fc oligonucleotide, site-directed mutagenesis was used to replace Glu 318, Lys 320, and Lys 322 of the C1q binding motif with Ala residues. Similarly, Leu 235 was replaced with Glu to inactivate the FcγR I binding site. Ligation of the IL-10 and Fcγ2a components in the correct translational reading frame at the unique Bam HI site yielded a 1,236 bp long open reading frame encoding a single 411 amino acid polypeptide (including the 18 amino acid IL-10 signal peptide) with a total of 13 cysteine residues (FIG. 1). The mature, secreted homodimeric IL-10/Fc is predicted to have a total of up to eight intramolecular and three inter-heavy chain disulfide linkages and a molecular weight of 90.1 kD, not accounting for glycosylation.

Expression and Purification of IL-10/Fc: Proper genetic construction of both IL-10/Fc++ (carrying the wild type Fcγ2a sequence) and IL-10Fc was confirmed by DNA sequence analysis following cloning of the fusion genes as Not I-Xba I cassettes into the eukaryotic expression plasmid pRc/CMV (Invitrogen, San Diego, Calif.). This plasmid carries a CMV promoter/enhancer, a bovine growth hormone polyadenylation signal, and a neomycin resistance gene for selection against G418. Plasmids carrying the IL-10/Fc++ or IL-10/Fc fusion genes were transfected into Chinese Hamster Ovary cells (CHO-K1, ATCC) by electroporation (1.5 kV/3 µF/0.4 cm/PBS) and selected in serum-free Ultra-CHO media (BioWhittaker Inc., Walkerville, Md.) containing 1.5 mg/ml of G418 (Geneticin, Gibco BRL). After subcloning, clones which produced the chimeric protein at high levels were selected by screening supernatants for IL-10 by ELISA (PharMingen, San Diego, Calif.). IL-10/Fc chimeric proteins were purified from culture supernatants by protein A sepharose affinity chromatography followed by dialysis against PBS and 0.22 µm filter sterilization. Purified proteins were stored at −20° C. until use.

Figures 2A, 2B:
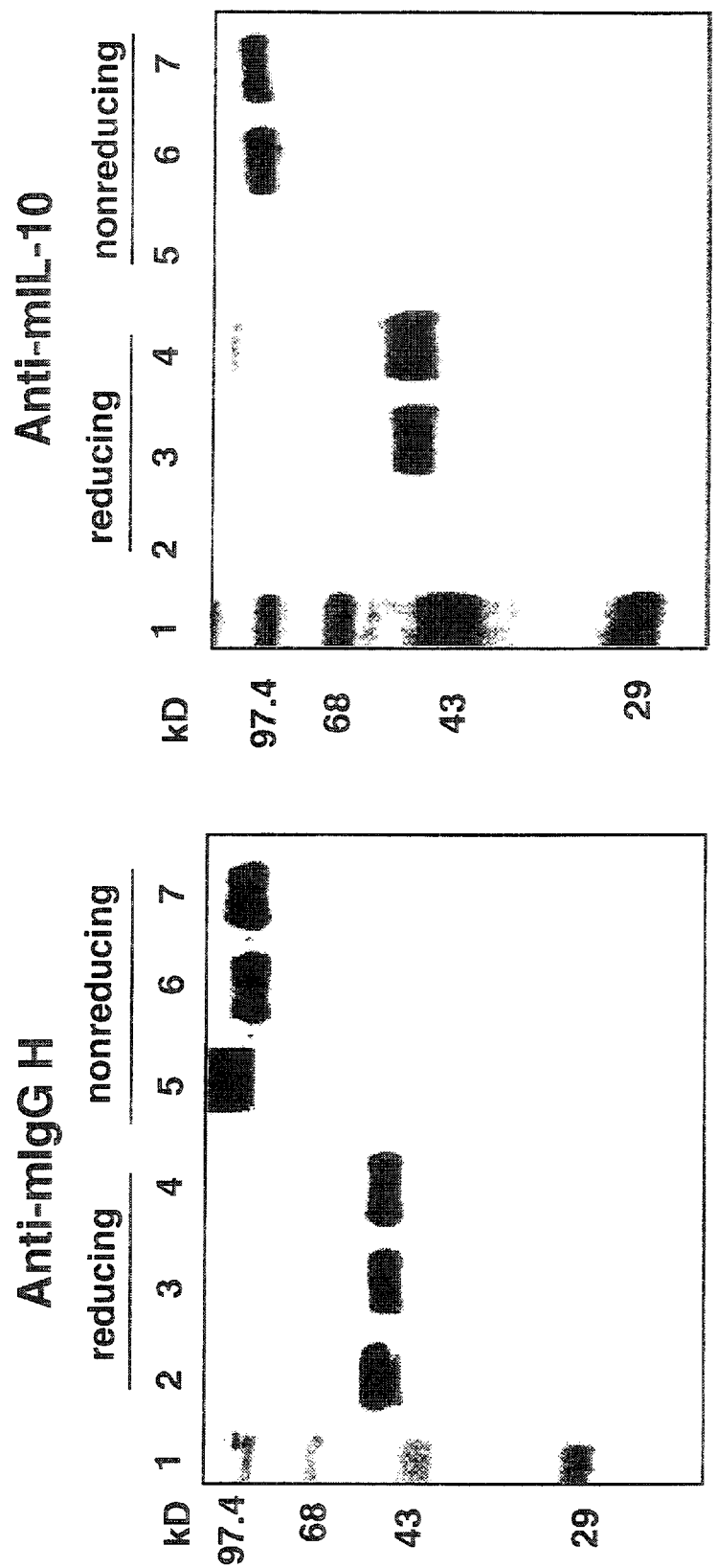

Confirmation of Size, IL-10 and Fcγ2a Isotype Specificity: Western blot analysis following SDS-PAGE under reducing (+DTT) and non-reducing (−DTT) conditions was performed using monoclonal anti-murine IL-10 (PharMingen) or polyclonal anti-murine Fcγ primary antibodies (Pierce, Rockford, Ill.). As is shown in FIG. 2, the IL-10/Fc chimeric protein each migrated under reducing (+DTT) conditions as a single species at the expected molecular size of 45 kD. Under non-reducing (−DTT) conditions, each IL-10/Fc migrated as a single species of molecular size of 91 kD, indicating that the chimeric proteins assembled as homodimers. Moreover, the IL-10/Fc fusion proteins bound both anti-mIL-10 mAb (FIG. 2B) and anti-mIgG heavy chain polyclonal antibodies (FIG. 2A), confirming the cytokine specificity of the IL-10 moiety and the isotype specificity of the Fcγ2a domain.

Standardization of the Biological Activity of rIL-10 and IL-10/Fc: Using the same RT-PCR strategy and 5' Not I sense oligonucleotide primer described above, mIL-10 cDNA with an Xba I restriction site added 3' to its native termination codon was cloned into pRc/CMV. This construct was then transiently expressed in COS cells (ATCC) by the DEAE dextran method and grown in serum-free UltraCulture media (BioWhittaker Inc.). At day 5, the culture supernatant was sterilized and stored at −20° C. to provide a source of rIL-10. Using a standard curve based on commercially supplied rIL-10 (PharMingen), IL-10/Fc and rIL-10 concentrations were determined by ELISA and then by bioassay. The unit activity based on ELISA corresponded with that obtained in a standard IL-10 bioassay, which utilized a murine mast cell line (MC/9, ATCC) with rIL-4 (PharMingen) as a co-stimulant (Thompson-Snipes et al., J. Exp. Med. 173:507 (1991)).

In Vitro Characterization of IL-10/Fc: IL-10/Fc functional activity was assessed in two independent assays. First, the ability of IL-10/Fc to inhibit IL-6 secretion by LPS-stimulated macrophages. In this assay, IL-6 (PharMingen) in the culture supernatants from murine monocyte/macrophage PU5-1.8 cells (ATCC) stimulated in the absence or presence of varying doses of rIL-10 or IL-10/Fc was measured by ELISA (Fiorentino et al., J. Immunol. 147:3815 (1991)). As is shown in FIG. 3, IL-10/Fc inhibits, in a dose-dependent manner, LPS-induced IL-6 secretion by PUS-1.8 cells.

Second, the ability of IL-10 to enhance the IL-4 dependent growth of the mast cell line MC/9 (ATCC) was assayed by measuring [$^3$H]-thymidine (New England Nuclear, Boston, Mass.) incorporation by these cells grown in 100 U/ml of rIL-10 or IL-10/Fc in the presence or absence of a neutralizing anti-murine IL-10 mAb (Biosource International, Camarillo, Calif.) (Thompson-Snipes, J. Exp. Med. 173:507 (1991)). FcγR I binding assays were performed using CHO-K1 cells transfected with human FcγR I cDNA. The murine FcγR I- and II-negative, IL-10 receptor-negative CHO cells were transfected by electroporation with 20 μg of Pvu I-linearized pRc/CMV carrying cDNA for human FcγR I (from Brian Seed, Massachusetts General Hospital, Boston, Mass.). CHO/FcγR I cells (5×10$^5$) were washed twice with FCM buffer (PBS containing 0.1% FCS (BioWhittaker Inc.) and 0.1% sodium azide (Sigma Chemical Company, St. Louis, Mo.) and then incubated with 10 μg/ml of murine IgG2a (Cappel, West Chester, Pa.), IL-10/Fc or IL-10/Fc++. After incubating for 60 minutes on ice, the cells were harvested and washed in FCM buffer and then incubated with fluorescein conjugated polyclonal goat-anti-mouse IgG Fc antibody (Pierce; Rockford, Ill.) for 60 minutes in the dark. The cells were washed and stored in a 1% formalin/PBS solution at 4° C. and then analyzed on a FACStar cell sorter (Becton-Dickinson, San Jose, Calif.). The data presented in FIG. 4 demonstrate that, as previously noted with rIL-10, IL-10/Fc enhances the IL-4-dependent growth of the murine mast cell line MC/9, and this costimulatory effect is blocked by a neutralizing anti-IL-10 mAb. Thus, on a mole for mole basis in terms of IL-10, IL-10/Fc possesses equivalent biological function as rIL-10 in these two bioassays.

Determination of IL-10/Fc Circulating Half-life: To measure the circulating half-life of IL-10/Fc, the serum concentration of IL-10/Fc was determined over time following a single bolus intravenous injection of the chimeric protein into each of six 8- to 10-week old BALB/c mice (Jackson Laboratory). Serial 100 μl blood samples were obtained by retro-orbital bleeding at 0.1, 6, 24, 48, 72, and 96 hours after administration of IL-10/Fc. Measurements employed an ELISA with a rat-anti-mouse IL-10 mAb as the capture antibody and horseradish peroxidase conjugated rat-anti-mouse Fcγ2a monoclonal antibody as the detection antibody (PharMingen), thus assuring that this assay was specific for IL-10/Fc and not IL-10 or mIgG2a. The circulating half-life of IL-10/Fc was determined to be 31 hours (FIG. 5). Thus the IL-10/Fc possesses the biological functions of IL-10 and a prolonged circulating half-life. Furthermore, due to the specific mutations introduced in Fcγ2a CH2 domain the FcγR I (Duncan et al., Nature 332–563 (1988)), binding abilities have been drastically attenuated (FIG. 6). In addition, we have found that the mutation in the C1q binding site greatly diminishes the ability of the Fcγ2a domain to activate complement. Therefore, the ability of IL-10/Fc to support CDC has been eliminated.

LPS-induced Septic Shock: To measure the ability of IL-10/Fc to treat or prevent septic shock, eight to ten week old BALB/c female mice were treated with IL-10/Fc, rIL-10, mIgG2a, or PBS prior to intravenous injection of 500 μg LPS (DIFCO, Detroit, Mich.). Groups of 12 animals each received 2000 U of IL-10/Fc or rIL-10 intraperitoneally 30 minutes before administration of LPS. In a second experiment each of 12 animals received 4000 U of IL-10/Fc or rIL-10 24 hours before administration of LPS. In control experiments, animals were treated with equivalent mass concentrations of mIgG2a (n=6) or volume of PBS (n=12) given 30 minutes before administration of LPS. Survival was the endpoint measurement.

As is shown in FIG. 7, a single dose of 500 μg LPS was uniformly lethal within 72 hours in animals pre-treated with PBS or mIgG2a. Mice treated with 2000 U of rIL-10 or IL-10/Fc 30 minutes before LPS challenge had a 50% survival rate. However, all mice treated with 4000 U of rIL-10 24 hours prior to LPS challenge died, while 50% of mice pretreated with 4000 U of IL-10/Fc survived. These data indicate IL-10/Fc and rIL-10 provide similar levels of protection from the lethal effect of LPS when they are given 30 minutes prior to an LPS injection. In contrast to rIL-10, IL-10/Fc confers prolonged protection, even when it is administered 24 hours prior to challenge with LPS. This finding is consistent with the longer circulating half-life of IL-10/Fc relative to rIL-10. Thus, these data indicate the chimeric molecule of the invention provides long-term protection against septic shock in a known animal model of the disease.

Other embodiments are within the following claims.

For example, virtually any mutation can be used to disable the complement-fixing capability of the Fc region of an antibody.

What is claimed is:

1. A chimeric protein comprising a mature IL-10 bonded to a polypeptide, said polypeptide comprising the Fc region of IgG, said Fc region of IgG having a circulating half-life by itself which is greater than that of IL-10.

2. The chimeric protein of claim 1 wherein said polypeptide comprises the Fc region of an IgG molecule.

3. The chimeric protein of claim 2 wherein said Fc region includes a mutation which inhibits complement fixation and Fc receptor binding by said protein, said mutation being a substitution mutation replacing at least one of the amino acids selected from the group consisting of Leu 235, Glu 318, Lys 320, and Lys 322 found in the murine CH2 domain.

4. A therapeutic composition comprising the chimeric protein of claim 1 admixed with a pharmaceutically acceptable carrier.

5. The chimeric protein of claim 2, wherein said Fc region is lytic.

6. The chimeric protein of claim 1, wherein said chimera increases the circulating half-life of IL-10 in vivo by a factor of at least 10.

7. The chimeric protein of claim 1, wherein said protein further comprises the hinge region of IgG.

* * * * *